US008777897B2

(12) United States Patent
Butterfield

(10) Patent No.: US 8,777,897 B2
(45) Date of Patent: Jul. 15, 2014

(54) FLUID DELIVERY SYSTEMS AND METHODS HAVING WIRELESS COMMUNICATION

(75) Inventor: Robert Dwaine Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 749 days.

(21) Appl. No.: 12/498,301

(22) Filed: Jul. 6, 2009

(65) Prior Publication Data
US 2011/0004186 A1 Jan. 6, 2011

(51) Int. Cl.
*A61M 31/00* (2006.01)

(52) U.S. Cl.
USPC .......................................................... 604/67

(58) Field of Classification Search
USPC ...................................................... 604/65–67
See application file for complete search history.

(56) References Cited

U.S. PATENT DOCUMENTS

| | | | |
|---|---|---|---|
| 5,563,584 A * | 10/1996 | Rader et al. ................... | 340/618 |
| 6,289,237 B1 | 9/2001 | Mickle et al. | |
| 7,175,081 B2 | 2/2007 | Andreasson et al. | |
| 7,361,155 B2 * | 4/2008 | Sage et al. ...................... | 604/65 |
| 7,413,123 B2 | 8/2008 | Ortenzi | |
| 2003/0040700 A1 | 2/2003 | Hickle et al. | |
| 2003/0236489 A1 | 12/2003 | Jacobson et al. | |
| 2004/0051368 A1 * | 3/2004 | Caputo et al. ................... | 299/1.9 |
| 2004/0176984 A1 | 9/2004 | White et al. | |
| 2005/0102167 A1 | 5/2005 | Kapoor | |
| 2006/0026205 A1 * | 2/2006 | Butterfield ................... | 707/104.1 |
| 2007/0100394 A1 | 5/2007 | Vasko | |
| 2007/0293817 A1 * | 12/2007 | Feng et al. ...................... | 604/65 |
| 2008/0033357 A1 | 2/2008 | Mann et al. | |
| 2008/0086086 A1 * | 4/2008 | Field et al. .................... | 604/123 |
| 2008/0240929 A1 | 10/2008 | Kamen et al. | |
| 2008/0312512 A1 | 12/2008 | Brukalo et al. | |

FOREIGN PATENT DOCUMENTS

| | | |
|---|---|---|
| EP | 1895437 A1 | 3/2008 |
| WO | 0236044 A2 | 5/2002 |
| WO | WO 2008008281 | 1/2008 |

OTHER PUBLICATIONS

PCT International Search Report, PCT/US2010/040661 International Searching Authority, European Patent Office, Aug. 23, 2010

* cited by examiner

*Primary Examiner* — Kevin C Sirmons
*Assistant Examiner* — Deanna K Hall
(74) *Attorney, Agent, or Firm* — McDermott Will & Emery LLP

(57) ABSTRACT

A fluid delivery system includes a disposable portion and a non-disposable portion configured to communicate with each other wirelessly. The disposable portion includes electrical elements such as one or more sensors configured to be in sensing proximity of fluid, a processor, a memory and a transceiver. The transceiver is configured to receive radio frequency energy from a transmitter located on the non-disposable portion and power the electrical elements on the disposable portion. The non-disposable portion wirelessly controls the disposable portion during a fluid delivery session by programming operational parameters and monitoring fluid delivery measurements over the wireless communication link.

20 Claims, 7 Drawing Sheets

FLUID DELIVERY SYSTEMS AND METHODS HAVING WIRELESS COMMUNICATION

FIELD

The present invention relates, in general, to fluid delivery systems and, more particularly, to a fluid delivery system in which sensor data is communicated wirelessly.

BACKGROUND

Intravenous (IV) fluid delivery systems are used to deliver fluid to a patient or to draw out fluid from a patient's body. A typical fluid delivery system includes a disposable portion attached to a non-disposable portion. In operation, fluid being delivered typically comes in contact with the disposable portion but is usually isolated from the non-disposable portion. Due to sterility and contamination concerns, the disposable portion is therefore typically discarded after use. On the other hand, since the non-disposable portion is generally fluidly isolated from the fluid being delivered through the system, it is therefore re-used for multiple fluid delivery operations. During a fluid delivery operation, fluid delivery parameters may be monitored using one or more sensors such as an air-in-line (AIL) sensor, a fluid pressure sensor, a fluid temperature sensor etc.

One operational issue of the sensors is that accuracy of measurement of fluid parameters may suffer because of the presence of an intervening isolating membrane. For example, a pressure sensor may produce inaccurate measurement results when an isolating membrane collapses due to negative fluid pressure. To overcome measurement inaccuracies caused by the isolating membrane, some prior art fluid delivery systems placed the sensor elements in contact with fluid being delivered. However, these systems require electrical wires running to the sensors and/or other electronics associated with the sensors to supply power. Due to the presence of electrical wires connecting the non-disposable portion to the sensor elements, such systems suffer from the drawback that accidental leakage from a sensor element could result in the fluid leaking along the electrical wires into the non-disposable portion, resulting in contamination and damage to the non-disposable portion. Furthermore, such placement of electrical wires in close proximity of fluids elevates the danger of accidental shocks to a patient connected to the fluid delivery system. Such shocks may be hazardous to the patients.

Hence, there are concerns regarding the current systems and methods for measuring fluid delivery parameters during fluid delivery by a fluid delivery system. These include, but are not necessarily limited to, accuracy of measurement and potential shock hazard.

SUMMARY

The above discussed and other concerns are fulfilled by fluid delivery systems and methods according to various configurations described in the present disclosure.

In one exemplary aspect, a disposable portion of a system for delivery of intravenous (IV) fluid, comprising a sensor configured to sense a fluid delivery parameter when positioned within a sensing range of the IV fluid; and a transceiver configured to wirelessly communicate with a non-disposable portion of a fluid delivery system is disclosed.

In a second exemplary aspect, a method of delivering fluid implemented at a processor of a fluid pump is disclosed. The method comprises performing a wireless scan to detect a disposable intravenous (IV) delivery set, loading, on the processor, the detected disposable IV delivery set to start a fluid delivery session, programming the detected disposable IV delivery set for operation with the fluid pump, and monitoring the fluid delivery session by wirelessly communicating with the IV delivery set.

In a third exemplary aspect, an apparatus for delivery of fluid, comprising a disposable portion comprising a sensor configured to measure a fluid delivery parameter, and a non-disposable portion that is fluidly isolated from the fluid, the non-disposable portion comprising a central processing unit (CPU) configured to wirelessly control an operational parameter of the sensor is disclosed.

The foregoing and other features, aspects and advantages of the embodiments of the present invention will become more apparent from the following detailed description and accompanying drawings.

DETAILED DESCRIPTION

The embodiments of the present disclosure address and solve problems related to the measurement of fluid parameters by providing, in part, a fluid delivery system having a disposable portion and a non-disposable portion configured to wirelessly communicate with each other. In one aspect, the disposable portion is configured to have no active electronics (power source) and is configured to wirelessly receive operational power from the non-disposable portion. In one aspect, a fluid delivery sensor is placed on the disposable portion.

Figure 1:
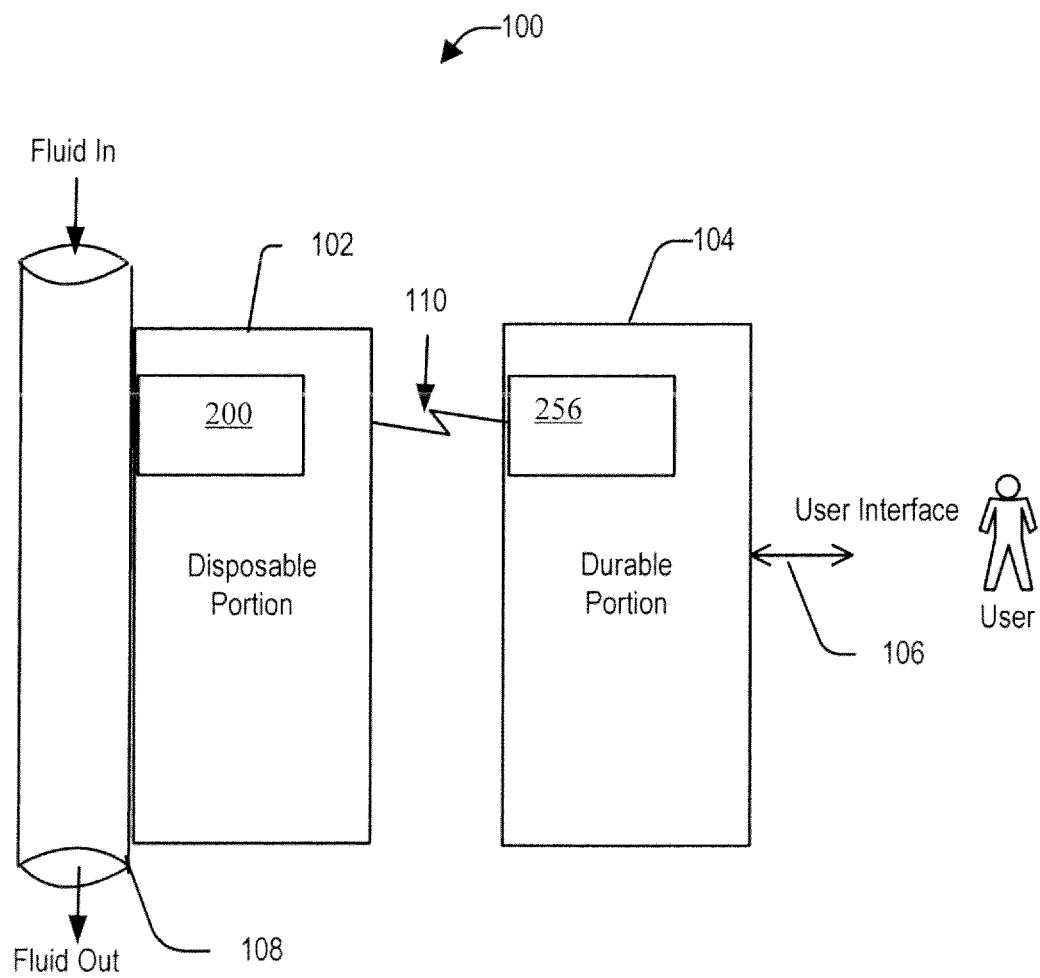
FIG. 1 is a block diagram depicting a fluid delivery system for use with embodiments of the present disclosure.

FIG. 1 shows a fluid delivery system 100 in accordance with certain configurations of the present disclosure. A disposable portion 102 comprises a fluid measurement system 200 and a non-disposable portion 104 comprises a fluid monitoring system 256. The disposable portion 102 and the non-disposable portion 104 are communicatively coupled via a wireless communication link 110. In addition, the disposable portion 102 and non-disposable portion 104 are configured to be fluidly isolated from each other, thereby avoiding any passage of fluid, accidental or intentional, from one portion to the other. The disposable portion is placed such that the fluid measurement system 200 is in sensing proximity to the fluid carrying tube 108. The non-disposable portion 104 is configured to communicate with a user via a communication link 106. By way of example and not limitation, in certain configurations, the disposable portion 102 is an intravenous (IV) fluid delivery set that is loaded into the non-disposable portion 104, which may be a large volume pump (LVP) module, such as the GEMINI® or the MEDLEY® product by Cardinal Health, Inc.

Still referring to FIG. 1, the wireless communication link 110 generally is operated at a frequency that does not interfere with other medical equipment in the vicinity. Similarly the communication frequency is chosen to avoid undesired interference from other wireless transmitters (e.g., wireless local area networking products) typically found in a hospital environment. In certain configurations, the physical distance between the disposable portion 102 and the non-disposable portion 104 is limited to a few centimeters. This lends itself to using a near field communication (NFC) technology for communication over the wireless communication link 110. While in most medical applications, a communication link 110 with approximately 100 kilobit/second data throughput may be sufficient, embodiments of the present disclosure are not limited to any specific range of data throughput. Short range communication such as the NFC technology described in the International Standards Organization's (ISO) ISO-14443 specification, may be advantageously used to avoid communication of a non-disposable portion 104 with disposable portions 102, other than the disposable portion 102 that is in close proximity (e.g., few centimeters). This avoids spurious connections between a disposable portion of one fluid delivery system with a non-disposable portion of another fluid delivery system in the vicinity. In certain configurations, a longer range wireless communication may be used, e.g., based upon the 802.1x suite of wireless standards specified by the Institute of Electrical and Electronics Engineers (IEEE).

Figure 2A:
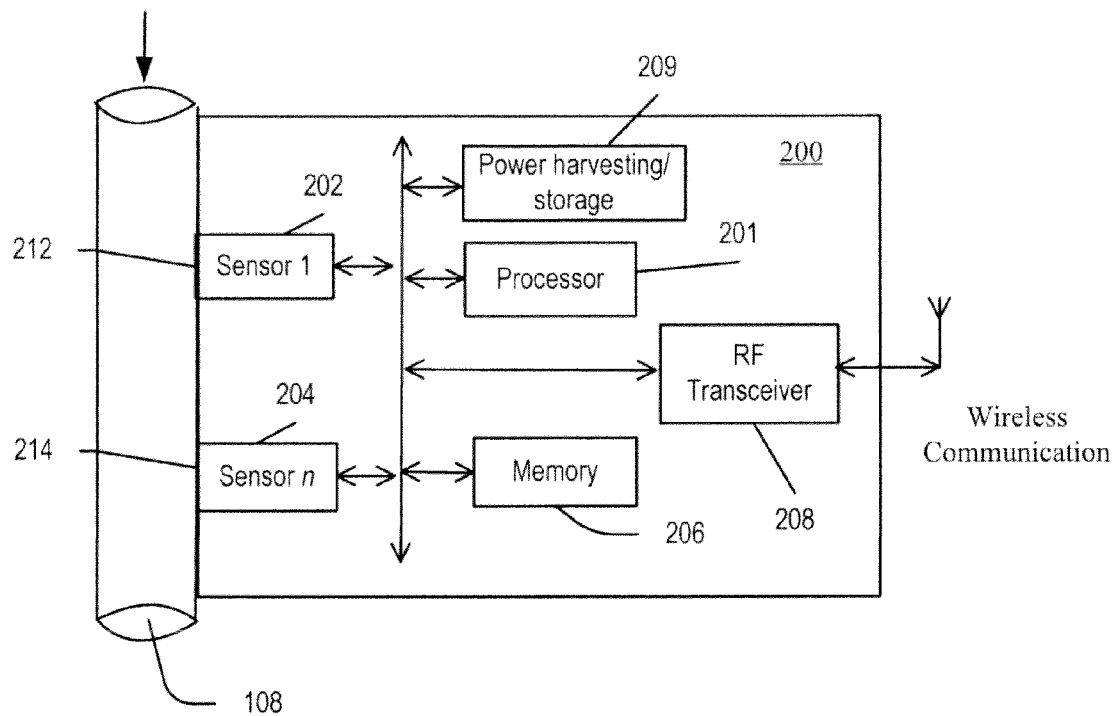
FIG. 2A is a block diagram depicting a fluid measurement system at a disposable portion, in accordance with certain configurations of the present disclosure.

FIG. 2A is a block diagram illustrating a fluid measurement system 200 implemented on the disposable portion 102 in accordance with certain configurations of the present disclosure. In the illustrated embodiment, the fluid measurement system 200 comprises a processor 201 communicatively coupled to a group of sensors including sensor 1 (element 202) to sensor n (element 204). In general, the number n is greater than or equal to 1. Sensor elements 202 and 204 may for example be, a fluid pressure sensor, a fluid temperature sensor, an air-in-line sensor, etc. The processor 201 is further communicatively coupled via a wired (Ohmic) connection with a memory 206 and a radio frequency (RF) transceiver 208.

Still referring to FIG. 2A, the sensors 202, 204 are configured to be in sensing contact with a fluid tube 108 at sensing regions 212 and 214 respectively. In certain configurations, a sensor element 202, 204 may be implemented to be in direct contact with fluid in the fluid tube 108, and the sensing regions 212 or 214 may be sealed (seal not shown in FIG. 2A) to prevent leakage of fluid. In certain configurations, an isolating membrane (not shown in FIG. 2A) may be provided at the sensing regions 212 or 214. The insulating membrane may act as a barrier preventing fluid leakage. The isolating membrane also protects sensor material from exposure to the fluid in the fluid tube 108. In certain configurations, some sensors are separated from the fluid by an isolating membrane while other sensors are configured to directly contact the fluid. In certain configurations, the RF transceiver 208 is further configured to radiatively receive energy to supply power to other electrical elements and for the operation of sensing fluid parameters. In certain configurations, the fluid measurement system 200 may be completely passive (i.e., not powered by a power source such as a battery).

Figure 2B:
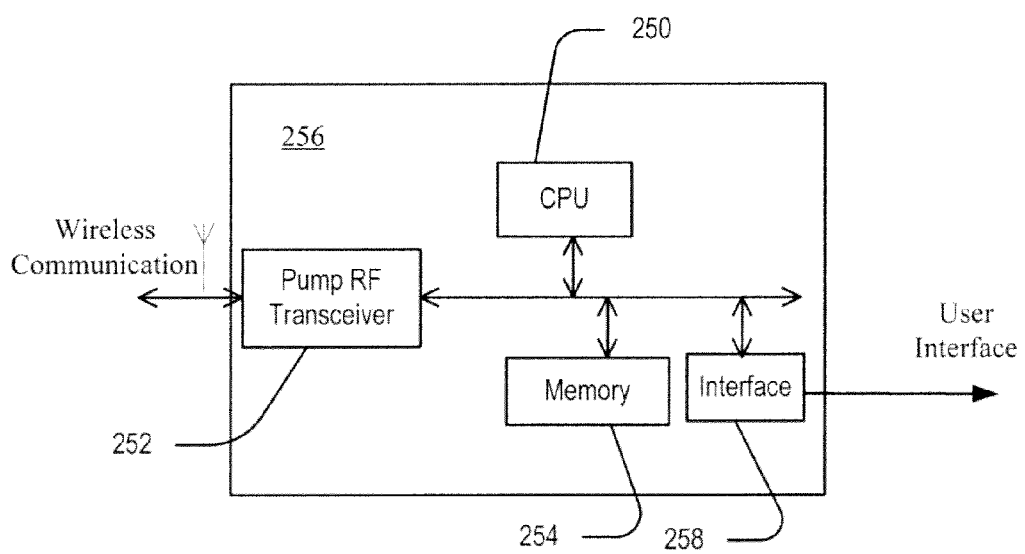
FIG. 2B is a block diagram depicting a fluid monitoring system at a non-disposable portion, in accordance with certain configurations of the present disclosure.

FIG. 2B is a block diagram illustrating portions of a pump fluid monitoring system 256, implemented at the non-disposable portion 104, in accordance with configurations of the present disclosure. The pump fluid monitoring system 256 comprises a pump RF transceiver 252, a central processing unit (CPU) 250, and a pump memory 254, all configured to communicate with each other. The pump fluid monitoring system 256 is further configured to communicate with a user and/or a network, either wired or wirelessly via interface 258, including receiving control messages from a user and reporting alarm and other messages to the user. The pump RF transceiver 252 communicates with the fluid measurement system 200 via the RF transceiver 208.

Figure 3:
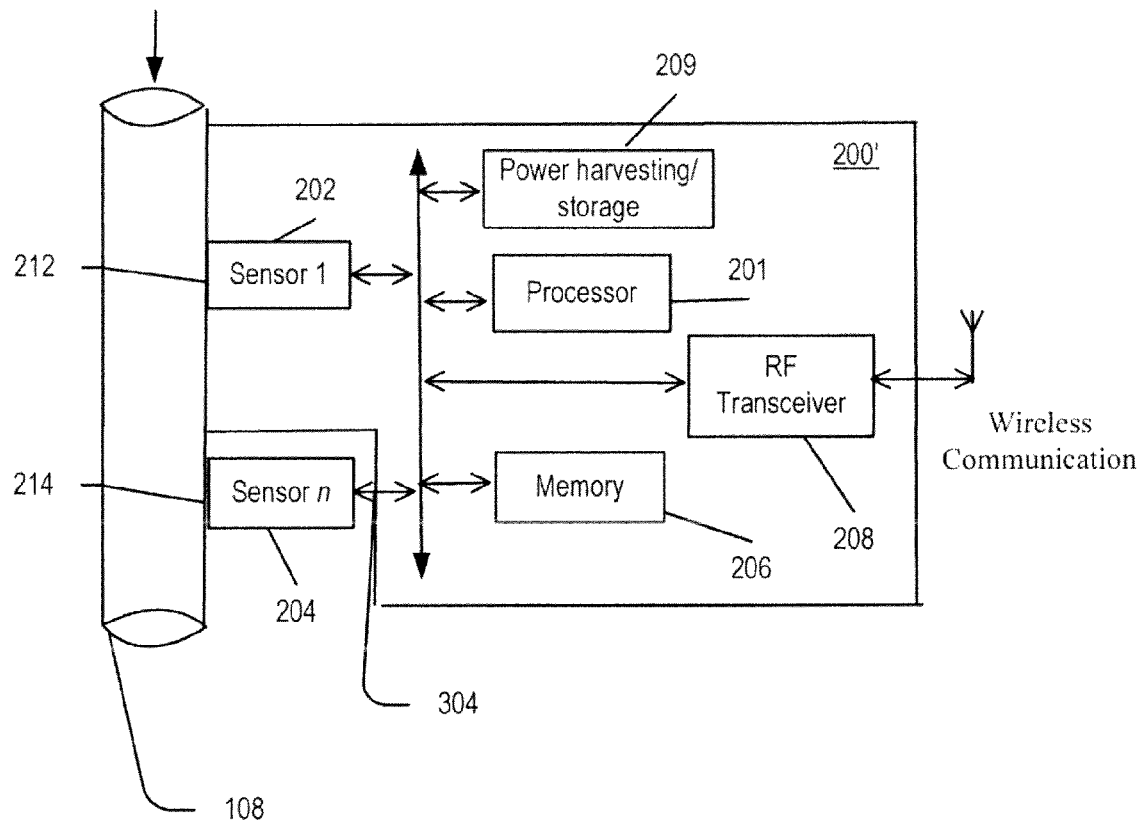
FIG. 3 is a block diagram depicting a fluid measurement system with an off-chip sensor, in accordance with certain configurations of the present disclosure.

FIG. 3 shows another exemplary configuration of the fluid measurement system 200, implemented on a disposable portion 102, in accordance with certain aspects of the present disclosure. As shown in FIG. 3, the processor 201 and one or more or all of the sensors 202, 204 of a group of sensors may be implemented on a single integrated circuit (IC) package 200' while some sensors may be provided external to the IC package 200' comprising the processor 201. In the configuration illustrated in FIG. 3, sensor n (element 204) is shown external to the IC package 200'. The sensor 204 is communicatively coupled with the processor 201 via an external connector 304. In certain embodiments, the connector 304 is implemented by vapor depositing conductive lines in the disposable portion 102. Such fabrication of connection to the sensor 204 advantageously enables miniaturization of the fluid measurement system 200' and also minimizes possibility of accidental leakage of fluid along the connector 304.

Figure 4:
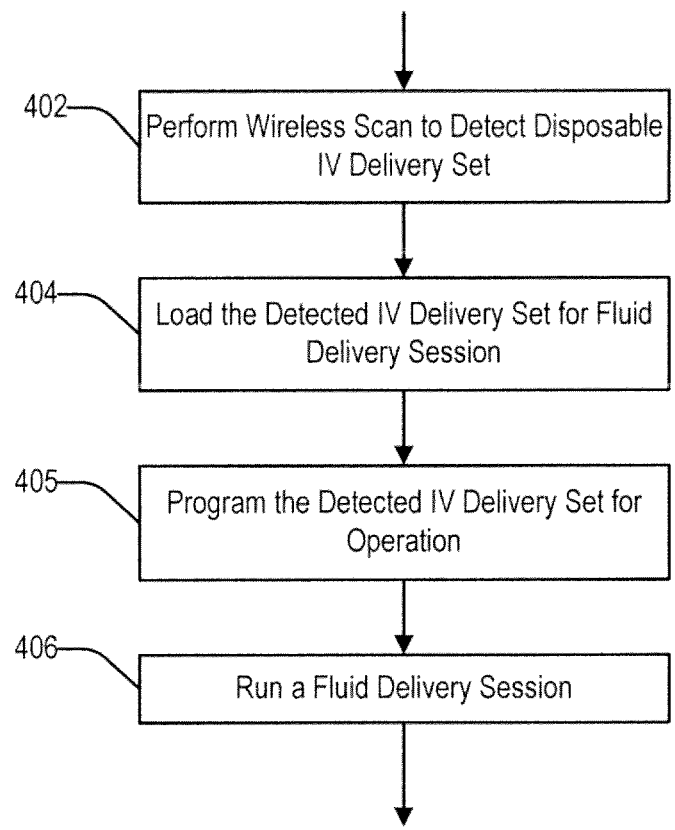
FIG. 4 is a flow chart depicting exemplary fluid delivery operations performed in accordance with certain embodiments of the present disclosure.

FIG. 4 shows an exemplary process implemented at a non-disposable portion 104. In certain embodiments, the process is implemented on the central processing unit (CPU) 250 provided at the non-disposable portion 104. In certain embodiments, the process is implemented at a computer in communication with the non-disposable portion 104 via interface 258. For example, in certain embodiments, the non-disposable portion 104 is a pump and the process is implemented at the CPU 250 on the pump 104. In certain embodiments, the non-disposable portion 104 is a part of a computer network located in a medical facility and may be communicatively connected to a patient-side computer or other computers in the medical facility. Exemplary medical facility communication networks are disclosed in U.S. Patent Pub. No. 20060026205 to Butterfield, incorporated herein by reference.

Still referring to FIG. 4, in operation 402, the CPU 250 performs a wireless scan to detect the presence of a disposable IV delivery set. The wireless scan may be performed using a variety of well known techniques. For example, in certain configurations, the CPU 250 scans for the presence of a disposable IV delivery set by transmitting a beacon signal and waiting for an answer from the IV delivery set in response to the beacon signal. In certain embodiments, the CPU 250 may detect presence of a disposable IV delivery set by sensing changes in electromagnetic fields around antennae attached to the transceiver 252.

In operation 404, the CPU 250 loads a detected IV delivery set to facilitate a fluid delivery session. The loading operation comprises identifying capabilities of the disposable portion 102 and verifying that the disposable portion 102 is suitable for a fluid delivery operation. In operation 404, the CPU queries an identification number from the disposable IV delivery set. In certain configurations, the identification number is used to maintain a usage log. In certain configurations, the processor 201 is configured to store and report total usage time. In certain configurations, during operation 404, the CPU 250 queries the processor 201 about total usage time and if the total usage time exceeds a time policy (e.g., as set by the hospital where the system 100 is deployed), then the CPU 250 may decide that the disposable portion 102 is not suitable for a fluid delivery session and terminate the loading operation 404 without performing the programming operation 405. The loading operation may further perform identification of operational parameters needed to be programmed before fluid delivery operation can be commenced. Example operational parameters include rate of sampling by a sensor, the amount of power required by a sensor, duration of operation by the detected disposable IV delivery set, etc.

Still referring to FIG. 4, in operation 405, the CPU 250 programs the detected disposable IV delivery set for operation. In certain configurations, the CPU 250 first reads back any operational parameters currently stored in the detected disposable IV delivery set. In certain configurations, the CPU 250 retrieves operational parameters for the detected disposable IV delivery set from another computer in a medical facility communication network using a unique identification number of the disposable IV delivery set. In certain embodiments, the CPU 250 is configured to receive a user input related to the operational parameters of the sensors located on the disposable IV delivery set. For example, in certain configurations, the CPU 250 is configured to first read an identification number for the detected disposable IV delivery set. Next, the CPU 250 retrieves range of allowable operational parameters for the detected IV delivery set from a hospital database located in the hospital communication network. Then, the CPU 250 facilitates display of the operational parameter, along with an allowable range adjustment to the user. Finally, the CPU 250 checks user input to ensure that the user input does not violate the allowable range of values for the parameter. In operation 406, the CPU 250 then transmits the operational parameters to the processor 201 and controls a fluid delivery session after programming the detected IV delivery set with the appropriate operational parameters.

Figure 5:
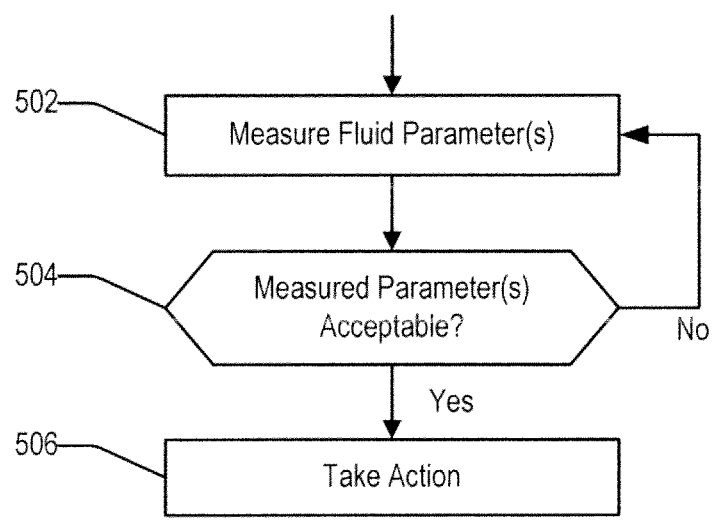
FIG. 5 is a flow chart depicting exemplary fluid delivery operations performed in accordance with certain embodiments of the present disclosure.

FIG. 5 shows an exemplary process implemented at operation 406 described above. In operation 502, the CPU 250 measures one or more fluid parameters. The CPU 250 performs the measurements by collecting measured sensory values from the sensors 202, 204 located on the disposable portion 102 (the detected IV delivery set). Accordingly, in one aspect of the present disclosure, the disposable portion 102 may be configured to wirelessly transmit measured values of fluid delivery parameters to the non-disposable portion 104. In certain configurations, the measurements are performed by the CPU 250 by communicating with the processor 201 and collecting fluid parameter values gathered by one or more sensors 202, 204 from the group of sensors. For example, in certain configurations, the CPU 250 detects the presence of air in the fluid tube by collecting sensory measurements from an AIL sensor. In certain configurations, the CPU 250 measures fluid pressure by collecting sensory measurements from a fluid pressure sensor. The CPU 250 specifies to the processor 201 the rate of sampling at which to make the measurements (e.g., one measurement per second). In certain configurations the measurements are polled by the CPU 250, i.e., the CPU 250 transmits a request to receive a measurement and the processor 201 responds by communicating back a measured fluid parameter value. In certain configurations, measurements are pushed to the CPU 250, i.e., the processor 201 may periodically sample sensors 202, 204 (e.g., based on operational parameters programmed in step 405) and transmit the sampled sensory values to the CPU 250. In certain configurations, sensory measurements may be periodically performed by both polling and pushing, as determined by the CPU 250.

In operation 504, the CPU 250 checks if a measured value (or values) does not meet an acceptability criterion. In certain configurations, the acceptability criterion is a range of allowable values. In certain configurations, the acceptability criterion is an acceptable minimum or maximum value threshold. In certain configurations, when the measured parameters are found to meet the acceptable criterion, the CPU 250 continues the fluid delivery session and further keep measuring fluid parameter values as in operation 502. If the measured parameter values do not meet an acceptability criterion, the CPU 250 takes an appropriate corrective action in operation 506. In certain configurations, the CPU 250 issues an alarm and displays to a user the measured value and the acceptable values for the parameter measured.

Figure 6:
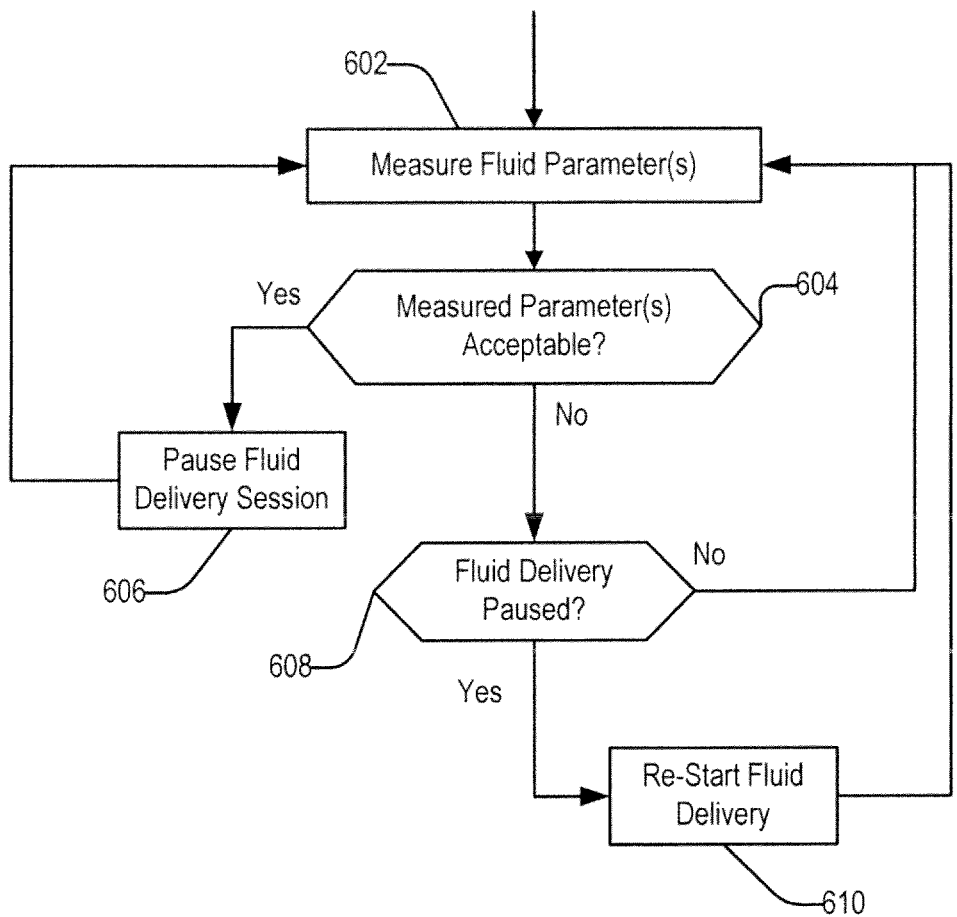
FIG. 6 is a flow chart depicting exemplary fluid delivery operations performed in accordance with certain embodiments of the present disclosure.

FIG. 6 shows an exemplary process implemented at the CPU 250. In operation 602, the CPU 250 measures a fluid parameter. At operation 604, the CPU 250 determines if the measured parameter value meets an acceptability criterion. If the measured value does not meet an acceptability criterion, the CPU 250 pauses the ongoing fluid delivery session in operation 606. The CPU 250 then returns to operation 602 and keeps measuring the fluid parameter. For example, the CPU 250 stops fluid delivery if a measured parameter value indicates presence of a specified amount of air in the fluid tube 108. The CPU 250 may still continue periodically making additional measurements from an AIL sensor.

Still referring to FIG. 6, if, at process 604, the CPU 250 measures a value from the additional measurements and determines that the measured value meets the acceptability criterion (e.g., an unacceptable amount of air is not present in the fluid tube 108), then the CPU 250 checks, in operation 608, if a fluid delivery session was paused. If a fluid delivery session was paused, then the CPU 250 re-starts the paused fluid delivery session in operation 610 and returns to operation 602 to measure fluid parameters. However, if in operation 608, a fluid delivery session was not paused, then the CPU 250 continues measuring flow parameters in operation 602.

Figure 7:
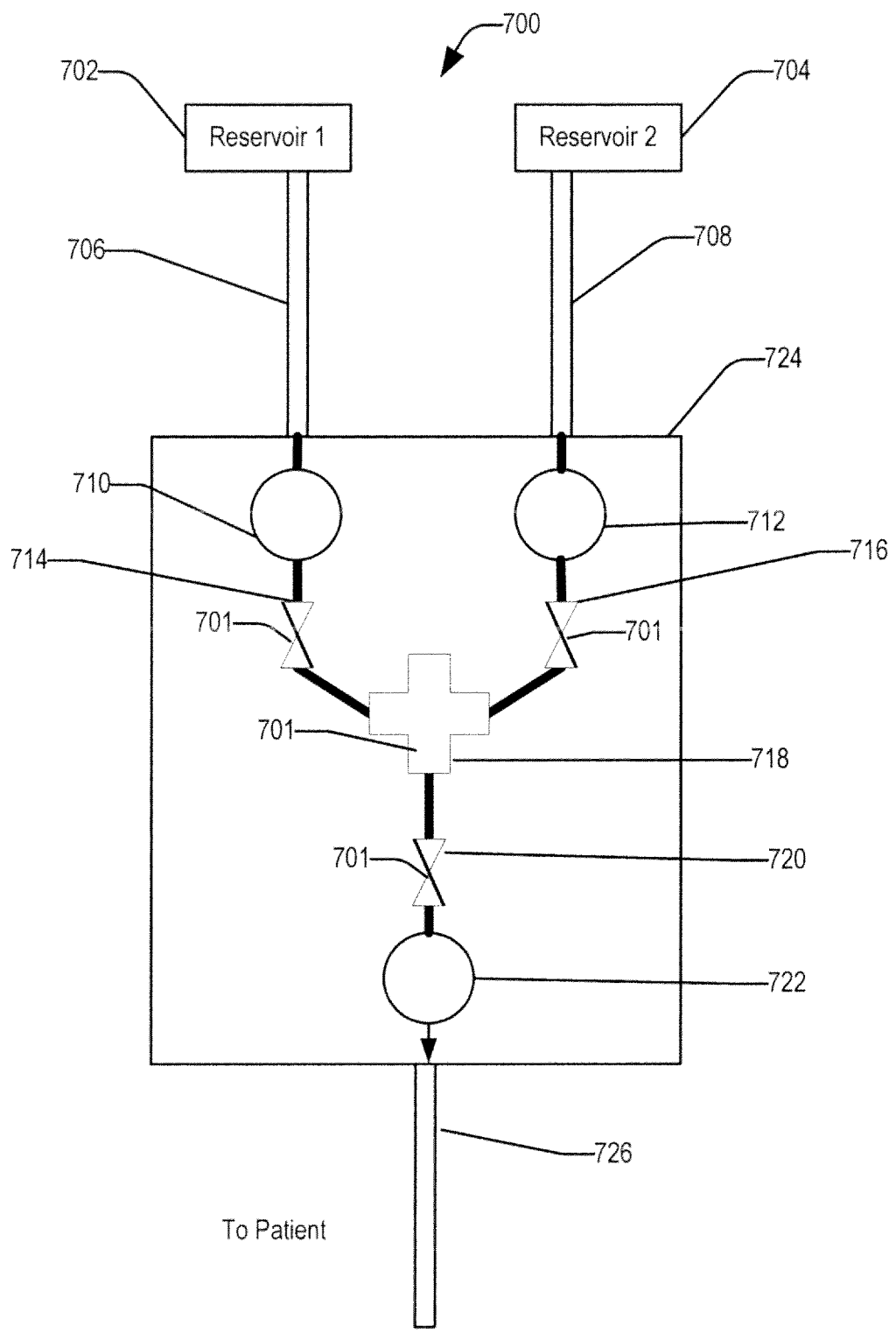
FIG. 7 is a block diagram of a fluid delivery system using embodiments of the present disclosures.

FIG. 7 shows a block diagram of an exemplary fluid delivery system 700 in accordance with certain aspects of the present disclosure. The fluid delivery system 700 comprises two reservoirs 702 and 704 attached to a pump enclosure 724. A first tube 706 is connected to reservoir 702 to all flow of fluid from the reservoir 702 to the valve 714. A second tube 708 is provided at reservoir 704 to allow fluid to flow from the reservoir 704 to flow to the valve 716. A first air-in-line (AIL) sensor 710 and a second AIL sensor 712 may be provided to detect air in the fluid flow from reservoirs 702 and 704 respectively. In certain embodiments, a single AIL sensor (not shown) may be provided, positioned between the valves 714 and 716 and the pump 718. Another AIL sensor 722 may be provided on the patient-side of the pump 718 after valve 720.

In operation, the fluid delivery apparatus 700 is used to deliver fluid from either one or both of reservoirs 702 and 704 to the patient side. The pump 718 controls the opening and closing of valves 714, 716 and 720 to move fluid from appropriate tubes 706, 708 to the patient side output 726.

Still referring to FIG. 7, in use, the fluid delivery system 700 may need to be back-primed. Back-priming refers to priming one fluid delivery tube (e.g., second tube 708) using fluid from another fluid delivery tube (e.g., first tube 706), while holding the patient side fluid tube (e.g., output 726) in a closed position. For example, referring to the illustrated fluid delivery system 700, a medical practitioner may use the fluid delivery system 700 to deliver fluid from reservoir 702, while turning off fluid reservoir 704. During this delivery from fluid reservoir 702 only, the fluid tube 708 may contain air. If the medical practitioner then wants to begin using fluid reservoir 704, the practitioner may be able to back-prime fluid tube 708 using fluid from tube 706 through the AIL sensor 710 and valve 714 by operating pump 718 so that the fluid does not flow to the patient side 726 during back priming. Because certain configurations of the present disclosure lend themselves to a small form factor implementation in which sensor elements and processor can be located on the disposable portion, the back-priming described above can be efficiently performed without the need for multiple wired connections between multiple AIL sensors on the disposable portion and the non-disposable portion.

In practice, it is common to sterilize medical equipment that comes in contact with medicine and vital fluids before using the medical equipment. The sterilization process typically involves exposing the medical equipment to a dose of gamma ray radiation. It is possible for electronics embedded within the medical equipment to become corrupted, e.g., malfunction or alter values stored in electronic memory. Accordingly, in certain aspects of the disclosed embodiments, the memory 206 comprises a portion configured to protect stored data from a radiative sterilization. For example, the memory 206, or a portion thereof is fabricated by a non-volatile semiconductor technology that resists damage due to exposure to gamma rays. Furthermore, the memory 206 may be configured to store critical information (e.g., identity of the system 200 such as a serial number) in an error correcting format. For example, a cyclic redundancy checksum (CRC) may be stored to allow detection and correction of any errors due to exposure to sterilizing radiation. In certain configurations, data may be redundantly stored at different addresses in the memory 206 and a verification check may be made to detect and correct errors while reading data.

In certain configurations, the processor 201 is programmed subsequent to the system 200 undergoing radiation exposure during sterilization. The programming is performed at a central location in a medical facility, or in situ, prior to use in patient-side equipment. Such programming after sterilization adds an additional level of ensuring data integrity by writing data to the memory 206 after exposure to radiation. The ability to wirelessly communicate with the processor 201 facilitates contactless programming of the processor 201, thereby avoiding possibility of medical contamination by physical contact with the disposable portion 102 during the programming. Furthermore, because data is wirelessly communicated, the processor 201 may be programmed speedily by eliminating the need to attach communication cables to the disposable portion 102.

It will be appreciated by those skilled in the art that the various embodiments described above provide advantageous fluid parameter measurement methods and systems. For example, in one aspect, because there is no conductive (Ohmic) contact between the disposable and non-disposable portions, the hazard of a patient inadvertently receiving a shock is mitigated. In another aspect, possibility of contamination of a non-disposable portion due to leakage of fluid from a disposable portion via a connecting wire during fluid delivery is avoided because no wires are required, both for communication and for power supply to the communication module located on the disposable portion. In another aspect, because power for operating the fluid measurement system on the disposable portion is provided wirelessly, the disposable portion does not need to have a power source, making it operationally easy to sterilize the disposable portion. Furthermore, in another aspect, data memory on the disposable portion is configured to protect from data loss due to exposure to sterilization. In another aspect, a disposable portion is configured to provide identification data to the non-disposable portion. In certain configurations, the identification data is advantageously used by the non-disposable portion to alert an operator of operational errors such as non-suitability of a disposable portion for a planned fluid delivery session.

By way of example, and not limitation, an exemplary configuration is now described in which a fluid delivery system comprises a disposable IV cassette having a fluid pressure sensor chip and a non-disposable fluid pump. A fluid pressure sensor, such as a Cobe CDXIII silicon gage sensor may be placed on the disposable portion 102. The same silicon package (sensor chip) that includes the sensor also includes a passive radio frequency identification (RFID) transceiver and an excitation and sensing circuitry to operate the sensor. An on-chip coil or another antenna is further integrated within the silicon package. The silicon package is then embedded within the body of a rigid IV cassette made of polycarbonate or acrylic. The pressure sensor is placed in sensing proximity of a the fluid channel 108, and is electrically and fluidly isolated from the fluid channel 108 by a small amount of silicone gel or similar material that conducts fluid pressure but also forms a dielectric barrier to prevent an electric connection. An RFID reader and antennae are placed in the fluid pump so that there is a very small distance between the antennae and the pressure sensor on the disposable portion. The small distance permits use of a high frequency excitation, able to transfer sufficient power to drive the pressure sensor. In operation, the reader periodically polls (by transmitting a radio frequency signal) the sensor chip. The sensor chip receives the radio power, rectifies it and stores on the chip (e.g., using a capacitor). The reception of power activates circuitry on the sensor chip which in turn activates the fluid pressure sensing mechanism to read a pressure. The voltage from the sensing mechanism is digitized, stored and transmitted using the RF transceiver to the reader on the non-disposable portion, which then processes and converts the digital data to a format for use by other monitoring circuitry, typically one of several processors communicatively coupled (e.g., via a hospital network) to the pump.

It is to be understood that the various operations described herein may be performed either in hardware, or software or in a combination thereof. The code for implementing such methods may be stored on a computer-readable medium, including but not limited to, distribution media, intermediate storage media, execution memory of a computer, and any other medium or device capable of storing for later reading by a computer a computer program implementing a method of this disclosure. Computer code implementing methods of this disclosure will be commonly stored and distributed on a floppy disk, a compact disc (CD) or a digital versatile disc (DVD). When the code is loaded on a computer, it causes the computer to execute methods and operations of the present disclosure.

Although embodiments of the present disclosure have been described and illustrated in detail, it is to be clearly understood that the same is by way of illustration and example only and is not to be taken by way of limitation, the scope of the present disclosure being limited only by the terms of the appended claims. Furthermore, one skilled in the art will recognize that while the present disclosure is generally described with reference to delivery of intravenous fluids in a patient care setting, certain configurations of the present disclosure may be used in non-clinical ex vivo applications such as laboratory experiments and medical device production facilities.

What is claimed is:

1. A disposable intravenous (IV) delivery set, comprising:
 a pumping portion configured to be loaded into a non-disposable IV pump;
 a sensor configured to sense a fluid delivery parameter when positioned within a sensing range of the IV fluid; and
 a transceiver coupled to the pumping portion and to the sensor, the transceiver configured to wirelessly communicate with the IV pump, the transceiver further configured to wirelessly receive energy from the IV pump and operate as well as provide operational power to the sensor solely from the wirelessly received energy.

2. The IV delivery set of claim 1, wherein the sensor is one of: fluid pressure sensor, an air-in-line detection sensor and a fluid temperature sensor.

3. The IV delivery set of claim 1, wherein the transceiver is configured to communicate using a near-field communication (NFC) protocol.

4. The IV delivery set of claim 1, further comprising a memory having a portion configured to protect stored data from a radiative sterilization.

5. The IV delivery set of claim 4, wherein the IV delivery set further comprises a processor communicatively coupled to the memory, the sensor and the transceiver.

6. The IV delivery set of claim 1, wherein the IV delivery set is configured to be fluidically and electrically isolated from the IV pump.

7. The IV delivery set of claim 4, wherein the memory comprises a unique identification value.

8. The IV delivery set of claim 5, wherein the processor and the sensor are implemented in a single integrated circuit (IC) package.

9. The IV delivery set of claim 5, wherein the sensor is external to an integrated circuit package comprising the processor; and the sensor is communicatively coupled with the processor via a connector external to the integrated circuit package.

10. The IV delivery set of claim 9, wherein the connector comprises a vapor deposited conductive wire.

11. A method of delivering fluid implemented at a processor of a fluid pump, the method comprising the steps of:
 performing a wireless scan to detect a wireless transceiver of a disposable IV delivery set that has been loaded into the fluid pump;
 loading, on the processor, the detected disposable IV delivery set to start a fluid delivery session;
 programming the detected disposable IV delivery set for operation with the fluid pump; and
 monitoring the fluid delivery session by wirelessly communicating with the IV delivery set.

12. The method of claim 11, wherein the monitoring step comprises periodically measuring one or more fluid parameters.

13. The method of claim 11, wherein the monitoring step comprises:
 if a measured fluid parameter value does not meet an acceptability criterion, then issuing an alarm.

14. The method of claim 11, wherein the monitoring step comprises:
 if a measured fluid parameter value does not meet an acceptability criterion, then pausing the fluid delivery session.

15. The method of claim 14, further comprising:
 periodically making additional measurements of the measured fluid parameter; and
 re-starting the fluid delivery session if any value from the additional measurements meets the acceptability criterion.

16. An apparatus for delivery of fluid, comprising:
 a disposable portion comprising:
  a fluid inlet;
  a fluid outlet fluidically coupled to the inlet;
  a sensor configured to measure a fluid delivery parameter at a point between the inlet and the outlet; and
  a wireless transceiver coupled to the sensor, the transceiver configured to wirelessly transmit measured values of the fluid delivery parameter; and
 a non-disposable portion configured to accept and physically couple to the disposable portion while remaining fluidically isolated from the fluid, the non-disposable portion comprising a central processing unit (CPU) configured to wirelessly control an operational parameter of the sensor.

17. The apparatus in claim 16, wherein the disposable portion is powered wirelessly by radio-transmitted energy from the non-disposable portion.

18. The apparatus of claim 16, wherein the disposable portion is further configured to wirelessly transmit an identification number to the non-disposable portion.

19. The apparatus of claim 16, wherein the CPU is further configured to receive a user input related to the operational parameter.

20. The apparatus of claim 16, wherein the operational parameter is a rate of sampling by the sensor.

* * * * *